(12) United States Patent
Chiang et al.

(10) Patent No.: US 8,559,687 B2
(45) Date of Patent: Oct. 15, 2013

(54) METHOD FOR CIRCULAR SCAN RECONSTRUCTION IN COMPUTED TOMOGRAPHY AND COMPUTED TOMOGRAPHIC DEVICE

(75) Inventors: Be-Shan Chiang, Buffalo Grove, IL (US); Alex Zamyatin, Buffalo Grove, IL (US); Mike Silver, Northbrook, IL (US); Yu Zou, Naperville, IL (US); Naruomi Akino, Tochigi-ken (JP); Thomas Labno, Algonquin, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 916 days.

(21) Appl. No.: 12/609,999

(22) Filed: Oct. 30, 2009

(65) Prior Publication Data

US 2011/0103662 A1    May 5, 2011

(51) Int. Cl.
*A61B 6/03*    (2006.01)
(52) U.S. Cl.
CPC ..................................... *A61B 6/03* (2013.01)
USPC ........................................................ 382/131
(58) Field of Classification Search
USPC ........................................................ 381/131
See application file for complete search history.

(56) References Cited

U.S. PATENT DOCUMENTS 6,282,256 B1 * 8/2001 Grass et al. ..................... 378/15
2010/0283779 A1 * 11/2010 Chiang et al. ................. 345/419

FOREIGN PATENT DOCUMENTS

WO    WO 2008064367 A2 *    5/2008

* cited by examiner

*Primary Examiner* — Toan Ton
*Assistant Examiner* — John Corbett
(74) *Attorney, Agent, or Firm* — Oblon, Spivak, McClelland, Maier & Neustadt, L.L.P.

(57) ABSTRACT

A method of computed-tomography and a computed-tomography apparatus where the portion of the field of view of a subject were full scan data is available is reconstructed using a full-scan algorithm. In the areas where full scan data is not available, half-scanning is used. Data is also extrapolated from the full scan data. The extrapolated data overlaps a portion of the half-scanning data. The extrapolated data and the overlapped portion of the half-scanning data are feathered. The image is reconstructed using the full-scan, half-scan and feathered data. Corner regions in an image are exposed and reconstructed to produce more uniform z-coverage of the reconstruction field of view.

21 Claims, 14 Drawing Sheets

METHOD FOR CIRCULAR SCAN RECONSTRUCTION IN COMPUTED TOMOGRAPHY AND COMPUTED TOMOGRAPHIC DEVICE

BACKGROUND OF THE INVENTION

1. Field of the Invention

The present invention relates to helical and circular x-ray computed tomographic (CT) imaging, and in particular to CT imaging with circular reconstruction with extended volume coverage and improved dose utilization.

2. Discussion of the Background

For computed tomography (CT), there are two main types of detectors: curved and flat, as shown in FIGS. 1A and 1B, respectively. The curved detector represents a cylindrical surface parallel to the z-axis (axis of rotation) and focused on the ray source. The flat detector represents a flat surface parallel to the z-axis. Even though detectors are physically placed at some distance D from the source, it is a common approach to consider a detector at distance R (radius of the source trajectory) from the source, so that detector contains the rotation axis.

The most commonly used reconstruction algorithm for circular cone beam CT is proposed in L. A. Feldkamp, L. C. Davis and J. W. Kress, "Practical cone beam algorithm," *Journal of Optical Society of America*, vol. 1 (6), pp. 612-619 (1984), hereinafter FDK. The algorithm uses full rotation of data, also called full scan (FS). Parker proposed a method where only π+FA, where FA is the Full detector fan angle opening. These parameters are not defined yet) of data angular range is used. D. Parker, "Optimal short scan convolution reconstruction for fan-beam CT," *Med. Phys.*, vol. 9, pp. 254-257 (1982).

The reconstruction volume for FS will be described with reference to FIGS. 2A and 2B. The field-of-view (FOV) 20 with a reconstruction pixel 21 at a distance r from the center of the FOV is scanned with x-rays at source to center distance R. The volume reconstruction region with circular scanning is limited in the z-direction by the divergent x-ray beam. A divergent x-ray beam does not cover the full z-extent of the FOV 20 on the source side, so that some corner parts of the FOV are not exposed at a particular view angle (see FIG. 2B). Thus, z-coverage is maximum at the center, and reduces at periphery, so that the reconstruction FOV has a hexagonal shape, illustrated by region 22 with the heavier lines in FIG. 2B. However, because the x-ray source rotates, the missing parts are covered by the x-ray beam when the source is on the opposite side.

The volume z-coverage at the distance r from the center is given by $$H_{FS}(r) = W\frac{R-r}{R} \quad (1)$$

W is the detector half-width at center. At the center (r=0) maximum z-coverage is obtained, with H=W. Moving away from the center, z-coverage linearly reduces. Note that in the case of the full scan, z-coverage is independent of detector type, i.e., flat or curved. A reconstruction pixel has polar coordinates (r, φ). Its short scan reconstruction range, denoted [$\beta_{start}$, $\beta_{end}$], is shown in FIG. 2C. FIG. 2D shows the z-coverage, where H(r) is the half-height of the volume z-coverage at the distance r from the center. The fan angle under which the reconstruction pixel is viewed from boundary views ($\beta_{start}$, $\beta_{end}$) is given by:

$$\gamma(r) = \arcsin\left(\frac{r}{R}\right) \quad (2)$$

View-range endpoints are given by:

$\beta_{start}(r,\phi) = \phi + \pi - \Delta\beta(r)/2$ $$\beta_{end}(r,\phi) = \phi + \pi + \Delta\beta(r)/2 = \beta_{start}(r,\phi) + \Delta\beta(r) \quad (3)$$

where $\Delta\beta(r)$ is the reconstruction view-range and is given by:

$$\Delta\beta(r) = \pi + 2\gamma(r) \quad (4)$$

The volume z-coverage at the distance r from the center in case of short scan with curved detector is given by:

$$H_{SS-CD}(r) = W\frac{d}{R} = W\cos\gamma(r) = W\frac{\sqrt{R^2-r^2}}{R} \quad (5)$$

The volume z-coverage at the distance r from the center in case of short scan with flat detector is given by:

$$H_{SS-FD}(r) = W\frac{d}{R/\cos\gamma(r)} = W\cos^2\gamma(r) = W\frac{R^2-r^2}{R^2}. \quad (6)$$

Volume z-coverage with different scans as a function of r is shown in FIG. 2E. Coverage for full scan (23), short scan with flat detector (24) and short scan with curved detector (25) are shown. For these curves, W=80 mm, and R=600 mm. Short scan provides much better z-coverage compared to the full scan, and the curved detector provides better coverage than the flat detector.

SUMMARY OF THE INVENTION

The present invention is directed to a computed-tomography method and apparatus. In one aspect, the method includes scanning an object with x-rays to obtain projection data, reconstructing a first part of an image of the object where full scan data is available, reconstructing a second part of the image using half-scanning where full scan data is not available, reconstructing a third part of the image using data extrapolated from the full scan data, combining weighted sums of overlapping portions of the second and third parts; and obtaining the image using the first to third parts and the combined weighted sums.

In another aspect, the computed-tomography apparatus includes an x-ray source, an x-ray detector, and a reconstruction processor for reconstructing an image of an subject from data collected by said x-ray detector. The processor reconstructs a first part of the image where full scan data is available, reconstructs a second part of the image using half-scanning data where full scan data is not available, reconstructs a third part of the image using data extrapolated from the full scan data, combines weighted sums of overlapping portions of the second and third parts, and reconstructs the image using the first to third parts and combined weighted sums.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1A:
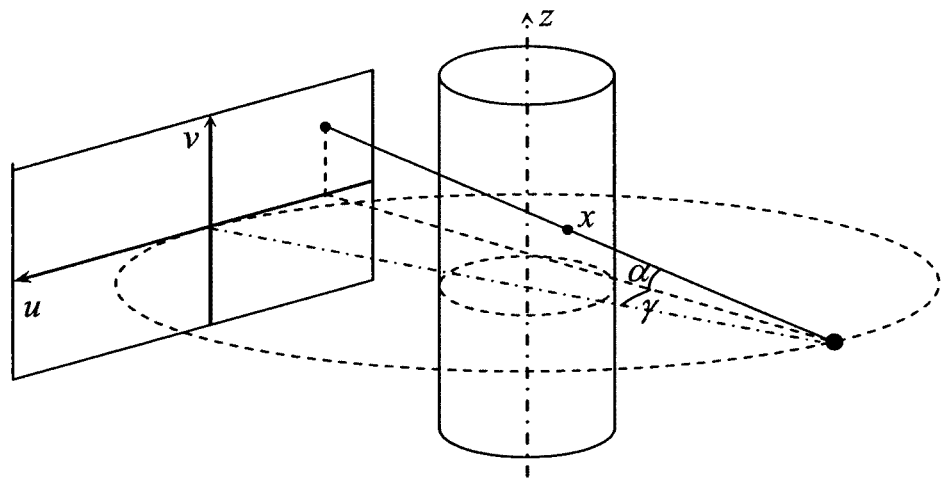
FIGS. 1A and 1B are diagrams illustrating computed tomography geometry with flat and curved detectors, respectively.
Figure 1B:
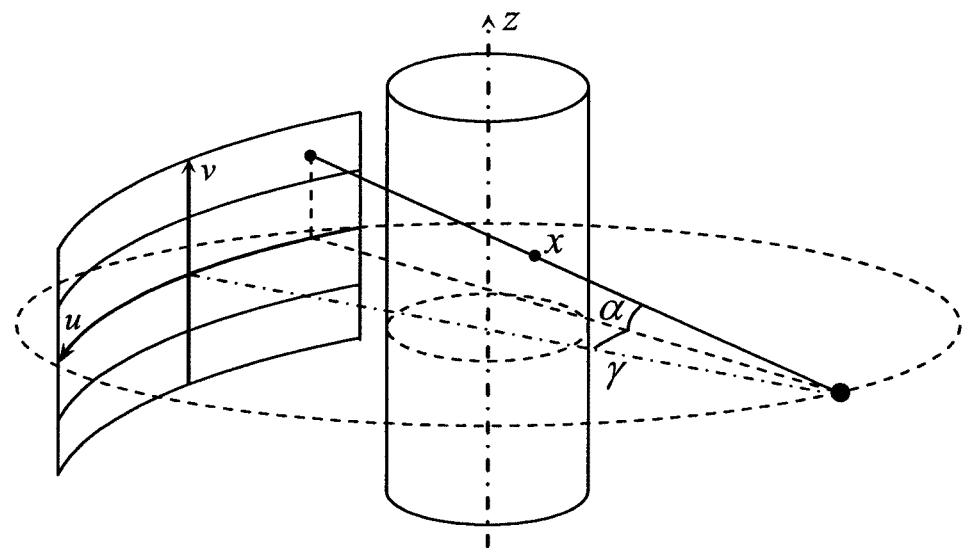
Figure 2A:
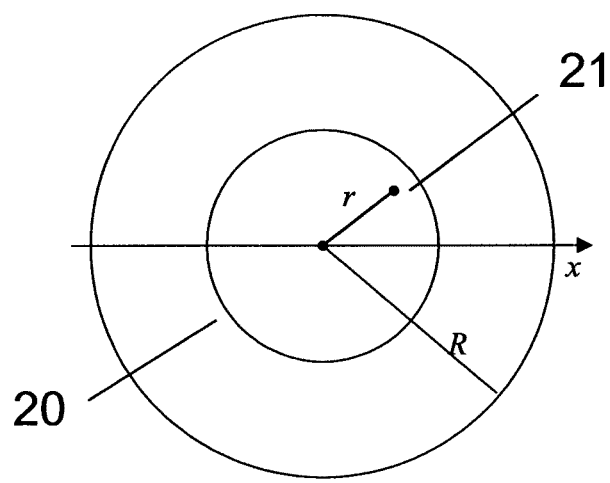
FIGS. 2A and 2B are diagrams illustrating a full scan reconstruction volume.
Figure 2B:
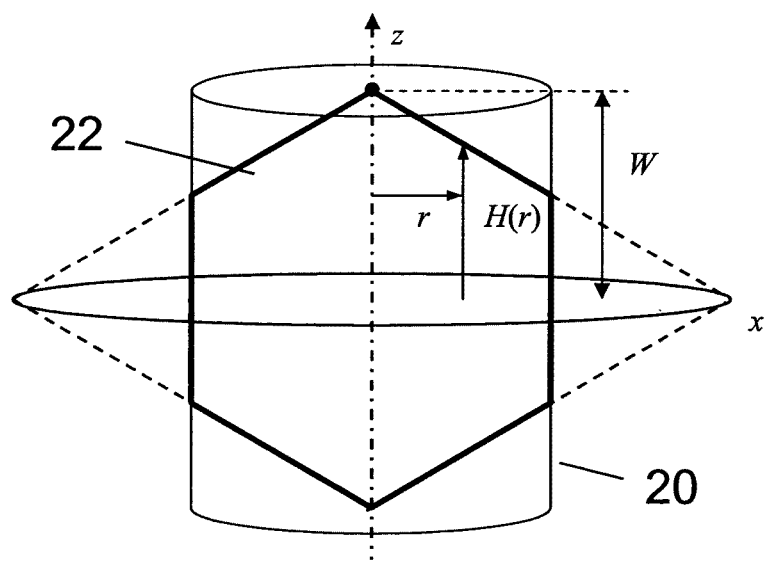
Figure 2C:
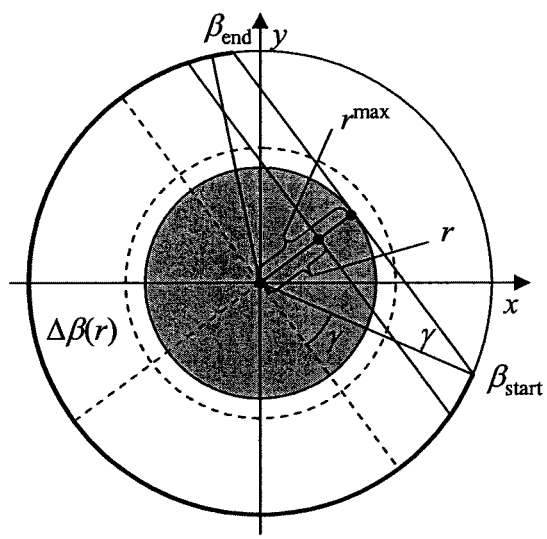
FIGS. 2C and 2D are diagrams illustrating half-scanning.
Figure 2D:
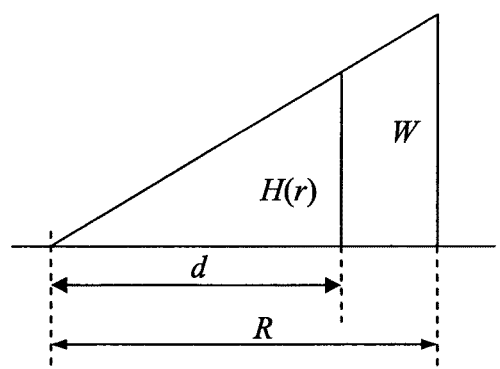

In a first embodiment of the invention, a subject is scanned in a circular trajectory for a plurality of scans to obtain circular image data over the subject. In circular scan reconstruction, the field-of-view (FOV) size in the z-direction is determined by the projection of the detector on the central axis. Typically, the volume reconstruction region with circular scanning is limited in the z-direction by the divergent x-ray beam. A divergent x-ray beam does not cover the full z-extent of the FOV on the source side, so that some corner parts of the FOV are not exposed at a particular view angle. Thus, z-coverage is maximum at the center, and reduces at the periphery, so that the reconstruction FOV has a hexagonal shape. This is shown in FIGS. 2A and 2B, with hexagonally-shaped FOV 22 of object 20 and corner regions 23. However, because the x-ray source rotates, the corner parts are covered by the x-ray beam when the source is on the opposite side.

Even though there is not enough data to reconstruct the corner parts of the FOV using the full-scan reconstruction, they can still be reconstructed using short-scan reconstruction. Each radial direction uses its own short-scan arc on the opposite side of the trajectory. The reconstruction according to the invention fully covers the FOV at the periphery, resulting in a full rectangular shape of reconstruction FOV and an improved image.

Figure 3:
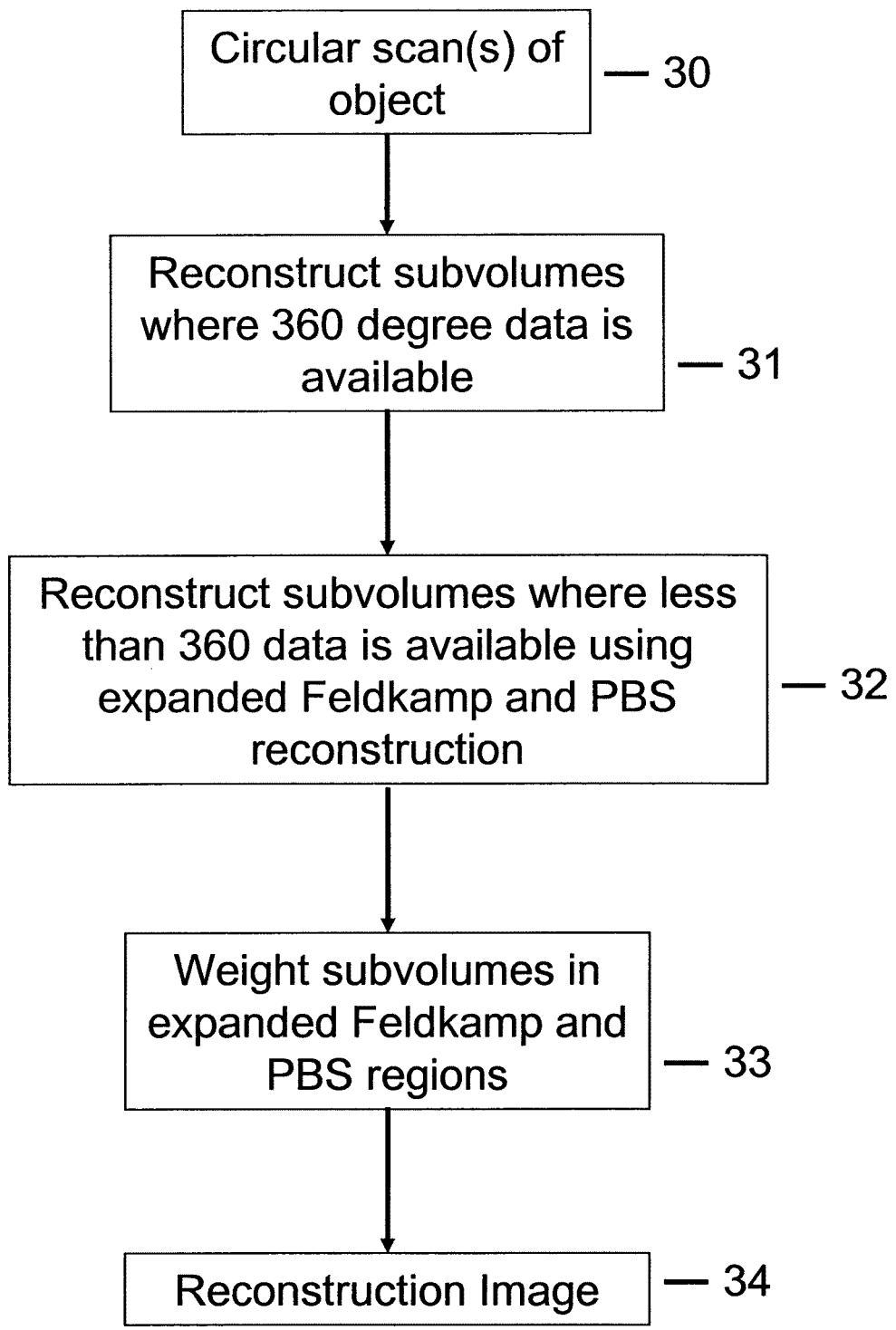
FIG. 3 is a flow diagram of an embodiment of the method according to the invention.
Figure 4:
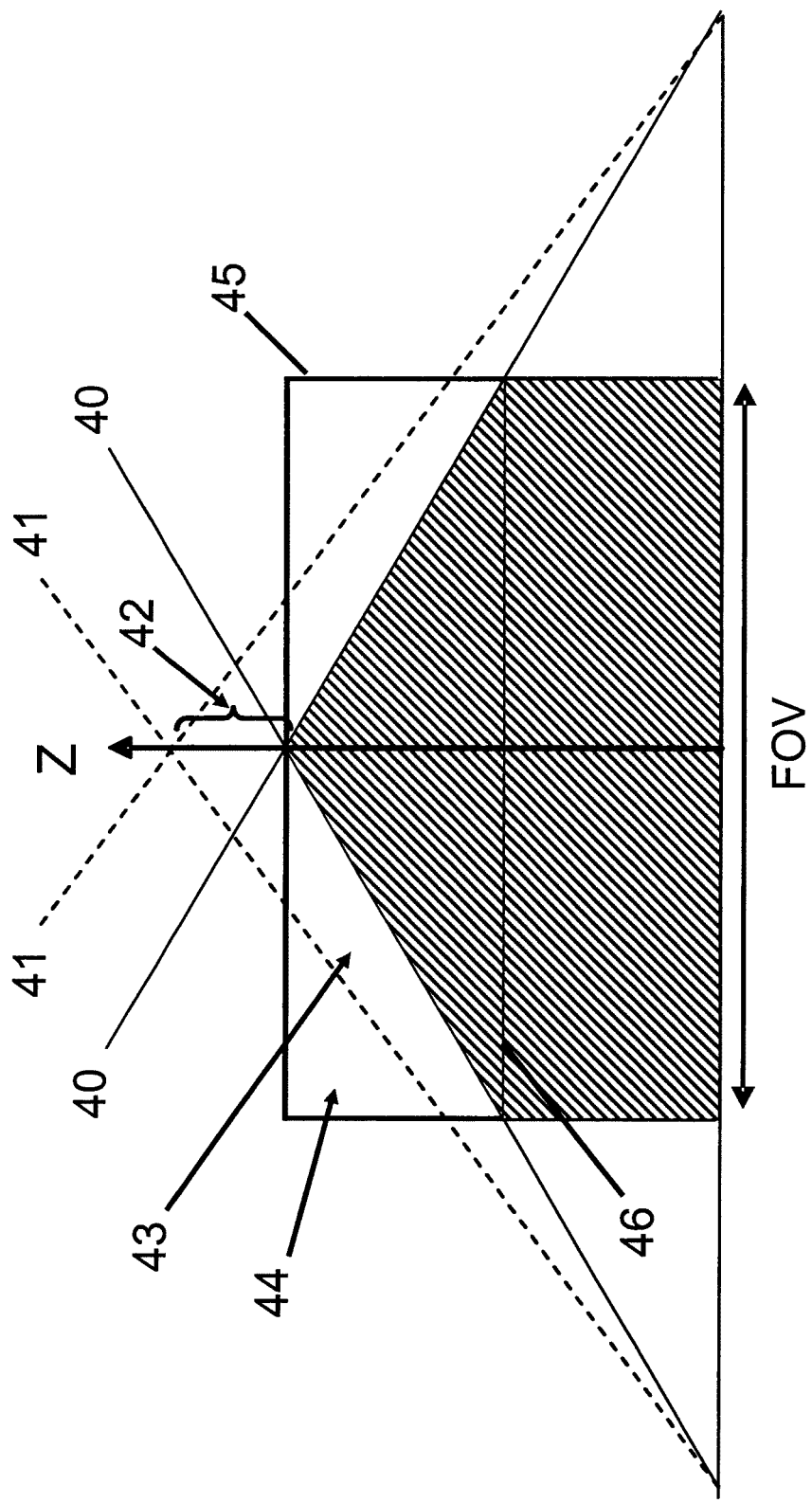
FIG. 4 is a diagram of scan geometry.

A first embodiment of the method according to the invention is shown in FIG. 3 and scans an object in a circular scan in step 30. FIG. 4 shows the geometry of the scan. The figure shows one half of the region scanned (FOV 45), with the fan angle indicated as lines 40. In the regions of the FOV 45 within the lines 40, shown in cross-hatch (i.e., 360 degree data is available), full-scan reconstruction is used. Dashed lines 41 define the regions where data can be extrapolated from expanded segments located in the z-direction at 42 and reconstructed. Data is extrapolated by known methods. Extrapolating more data introduces more errors. When less data is used in extrapolation, there can be a jump in pixel values, producing a discontinuity in the image.

Reconstruction in the corner regions is performed using a reconstruction process termed Pixel-Based Sector (PBS) reconstruction (described in more detail below). PBS reconstruction is used in regions 43 and 44, and extrapolated data is reconstructed in region 43. In the PBS approach, each image pixel has its own short-scan (SS) reconstruction view-range. Pixels on a radial ray share the same short scan view-range. However, in discrete image coordinates it is unlikely that any two image pixels will belong to the same radial ray, and therefore the short-scan weighting function is computed for image pixels. Such sector assignment allows the best possible data utilization and leads to improved image quality.

For slices in the FOV from z=0 up to the line shown as 46, 360 degree data is available and full scan reconstruction is used (step 31). From line 46 up to the top of the FOV, a combination of full scan, expanded full scan and PBS reconstruction are used (step 32). In the regions 43, where expanded full scan and PBS reconstruction overlap, the image subvolumes are weighted using a weighting function (step 33), which is described in more detail below. In a preferred manner, the expanded full scan and PBS reconstructed subvolumes are feathered. The image is reconstructed from the various reconstructed subvolumes and weighting (step 34).

Figure 5A:
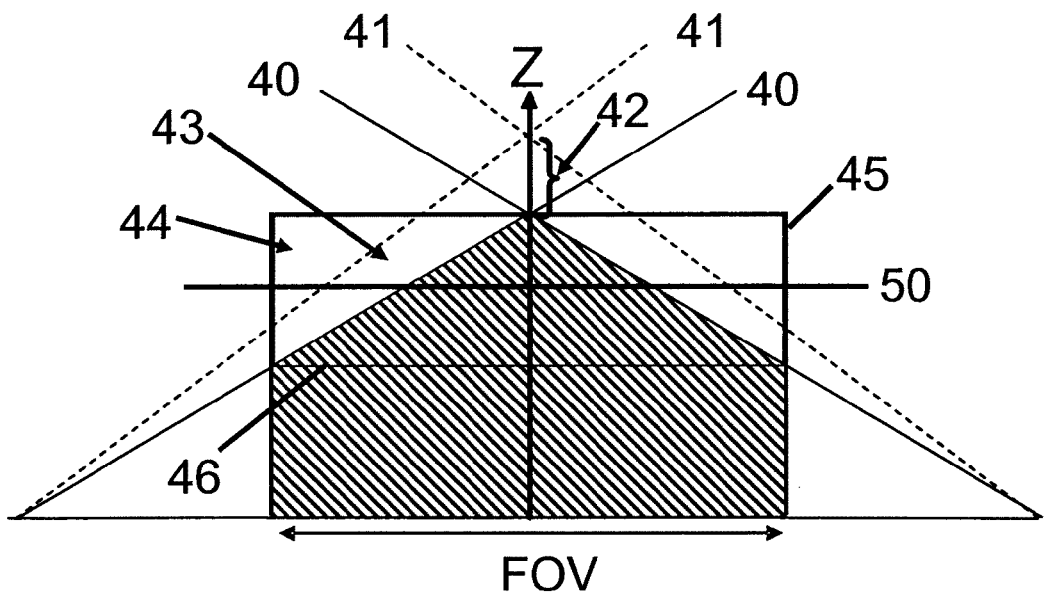
FIGS. 5A and 5B show the regions of reconstruction for a slice of an FOV having a circular cross-section.
Figure 5B:
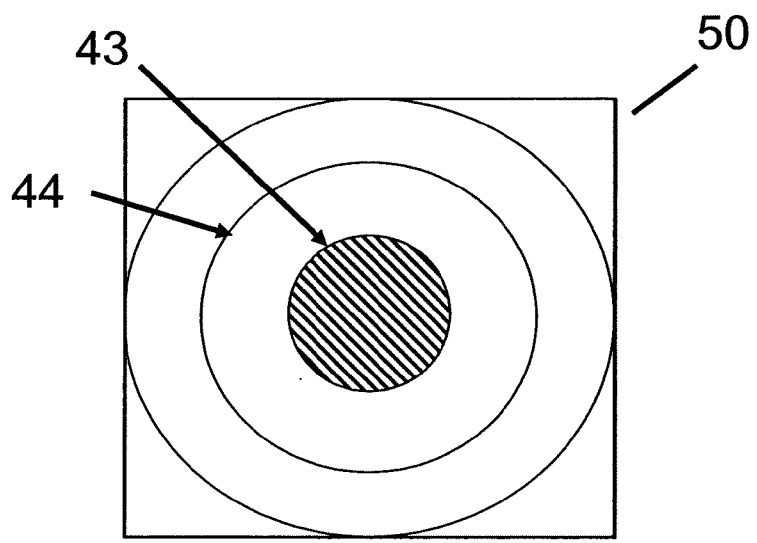

FIGS. 5A and 5B show the regions of reconstruction for a slice 50 for an FOV having a circular cross-section intersecting the full scan (cross-hatched) region and regions 43 and 44. It is noted that any shape FOV may be used with the method according to the invention.

In more detail, given a reconstruction pixel $\bar{x}(x,y,z)$, its polar coordinates are given by:

$$r = \sqrt{x^2 + y^2} \quad (7)$$

$$\varphi = \arctan\left(\frac{y}{x}\right)$$

The full-scan reconstruction region is given by:

$$\Omega_{FS} = \{(x,y,z) \| |z| \leq H_{FS}(r(x,y)) \}, \quad (8)$$

where $H_{FS}(r)$ is given by (1). The half-scan reconstruction region is given by:

$$\Omega_{HS} = \{(x,y,z) \| |z| \leq H_{HS\text{-}CD}(r(x,y)) \} \quad (9)$$

where $H_{HS\text{-}CD}(r)$ is given by (5). Note that $\Omega_{FS}$ is a subset of $\Omega_{HS}$, and the extended region is given by difference $$\Omega_{EXT} = \Omega_{HS} - \Omega_{FS}. \quad (10)$$

If a reconstruction pixel belongs to the full-scan region (i.e., $\bar{x} \in \Omega_{FS}$) then the full-scan algorithm may be used as described in A. A. Zamyatin, K. Taguchi and M. D. Silver, "Practical Hybrid Convolution Algorithm for Helical CT Reconstruction," *IEEE Transactions on Nuclear Sciences*, vol. 53, no. 1, pages 167-174, which is herein incorporated by reference:

$$f(\bar{x}) = \frac{1}{4\pi} \int_0^{2\pi} \frac{1}{L(\beta, \bar{x})} Q_0[g(\beta, \gamma, \alpha)]\Big|_{\substack{\gamma=\gamma(\beta,\bar{x}) \\ \alpha=\alpha(\beta,\bar{x})}} d\beta, \quad (11)$$

where $Q_0[\cdot]$ is the DC-adjusted ramp convolution as described in Zamyatin et al. and $L(\beta, \bar{x})$ is the distance between the source $y(\beta)$ and pixel $\bar{x}$. Alternatively, full scan Feldkamp reconstruction may be used.

If a reconstruction pixel belongs to the extended region (i.e., $\bar{x} \in \Omega_{EXT}$) then the short-scan algorithm described in Zamyatin et al. is used:

$$f(\bar{x}) = \frac{1}{2\pi} \int_{\beta_{start}(\bar{x})}^{\beta_{end}(\bar{x})} \frac{w_N(\beta, \bar{x})}{L(\beta, \bar{x})} K[g(\beta, \gamma, \alpha)] \Big|_{\substack{\gamma = \gamma(\beta, \bar{x}) \\ \alpha = \alpha(\beta, \bar{x})}} d\beta, \quad (12)$$

where K[•] denotes the hybrid convolution as described in Zamyatin et al. and $w_N$ denotes [a weighting function (described in more detail below)].

Figure 2E:
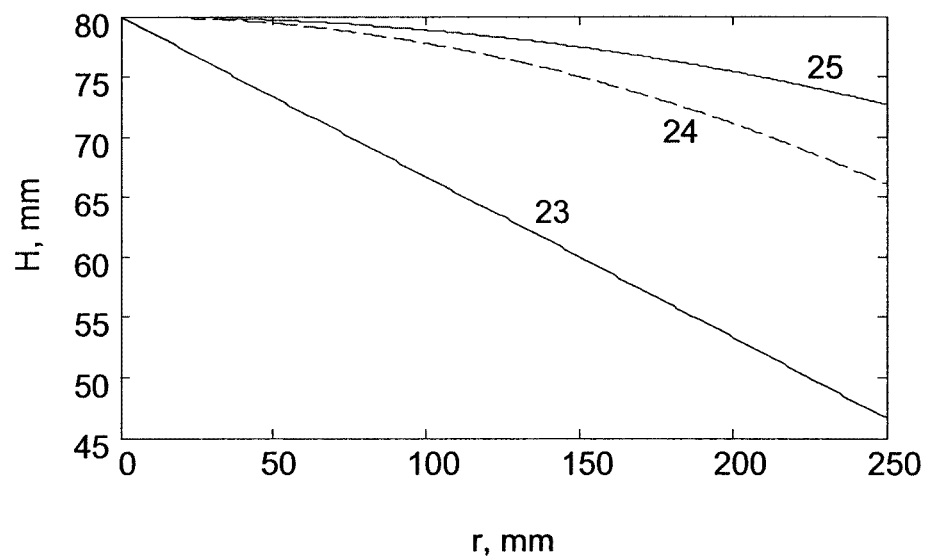
FIG. 2E is a diagram of volume z-coverage with different scans as a function of distance from the center.

The first embodiment will be described in more detail. Note that equations (3) above define a 1π view range, i.e., the minimum view range. These equations are useful to find the region where short scan reconstruction without extrapolation is possible. However, a larger short scan range (up to 2π) may be used. Including more data into reconstruction reduces noise and cone beam artifacts. Thus, the maximum short scan range as a function of image slice z-position and r is derived. FIG. 2E illustrates volume coverage for different values of r. At the line 23, a 2π view range is available, while at lines 24 (straight detector) and 25 (curved detector) a 1π view range is available. The available view range varies from 1π to 2π between line 23 and line 24/25.

Figure 6A:
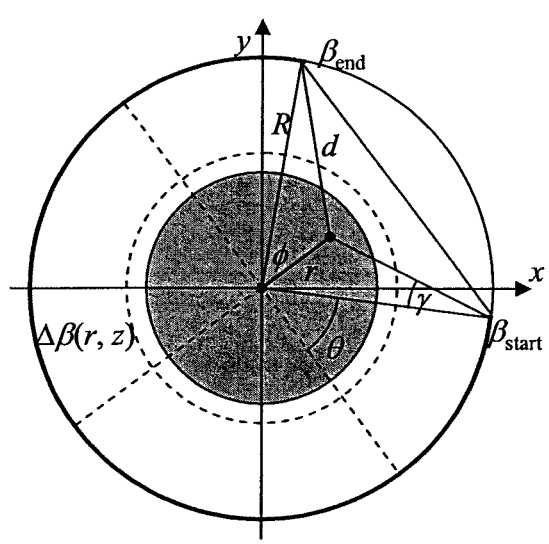
FIGS. 6A and 6B illustrate the view-range in half-scanning.
Figure 6B:
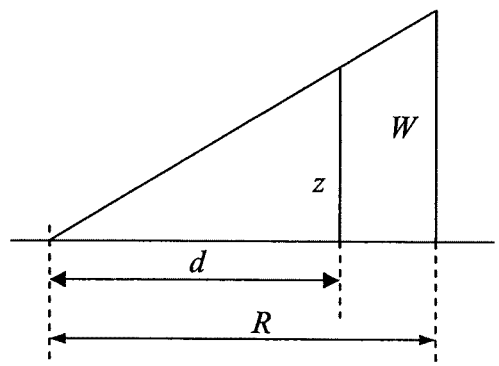

As the trajectory arc wraps around the image slice, projection cone angles increase. For given z and r the reconstruction view-range [$\beta_{start}$, $\beta_{end}$] is determined by the value d, as shown in FIGS. 6A and 6B. This value is given by:

$$d = R \frac{z}{W} \quad (13)$$

that is, d is the shortest distance at which the source can approach the pixel (r, φ) without projecting outside of the detector. From FIGS. 6A and 6B the extended view-range is given by:

$$\beta_{start}(r, \phi, z) = \phi + \pi - \Delta\beta(r, z)/2$$

$$\beta_{end}(r, \phi, z) = \phi + \pi + \Delta\beta(r, z)/2 = \beta_{start}(r, \phi, z) + \Delta\beta(r, z) \quad (14)$$

$$\Delta\beta(r, z) = \pi + 2\theta \quad (15)$$

$$\theta = \frac{\pi}{2} - \phi, \ \phi = \arcsin\left(\frac{d}{R}\sin\gamma\right) \quad (16)$$

$$\gamma = \arccos\left(\frac{r^2 + d^2 - R^2}{2rd}\right) \quad (17)$$

Or, after some simplifications the following equations are obtained:

$$\Delta\beta(r, z) = 2\pi - 2\phi \quad (18)$$

$$\phi = \arcsin\left(\frac{\sqrt{(R^2 - (r-d)^2)((r+d)^2 - R^2)}}{2Rr}\right) \quad (19)$$

Figure 7A:
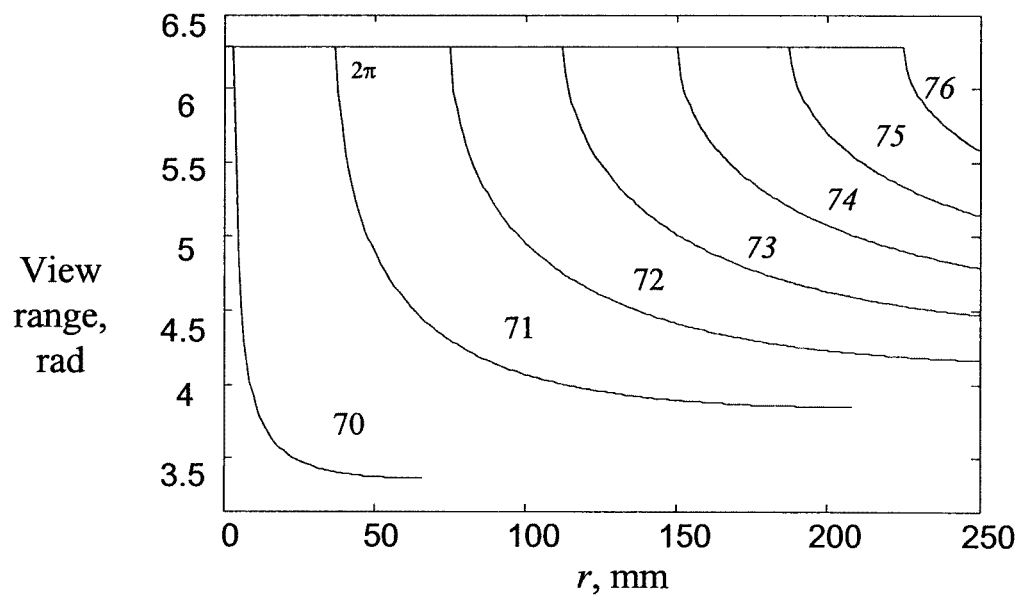
FIG. 7A shows the view range in radians as a function of radial distance.
Figure 7B:
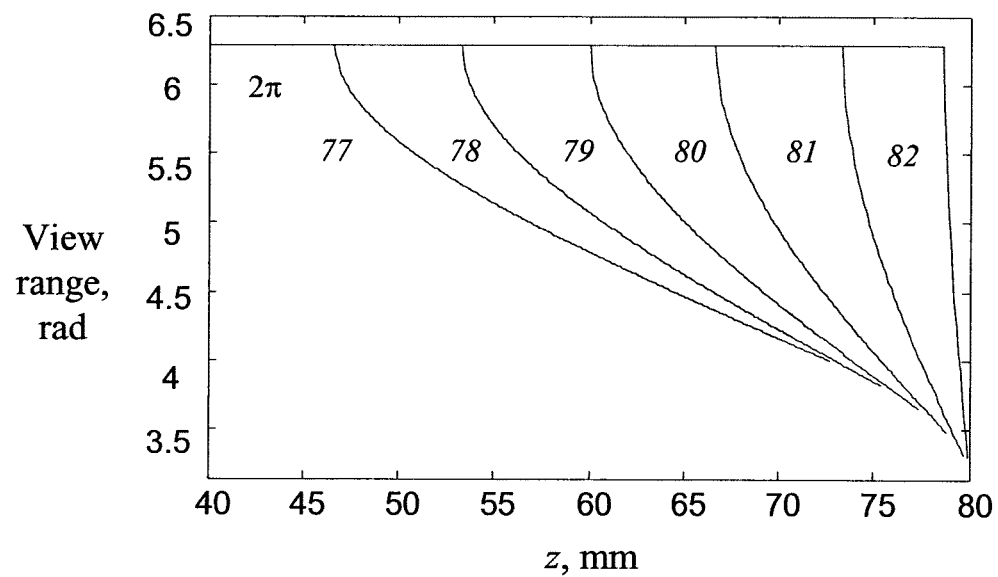
FIG. 7B shows the view range in radians as a function of z.

FIG. 7A shows the view range in radians as a function of r. The curves 70-76 are for values of r of 79.5, 75, 70, 65, 60, 55 and 50, respectively. FIG. 7B shows the view range as a function of z. Curves 77-82 respectively correspond to values of r of 250, 200, 150, 100, 50 and 10.

Each image pixel is given its own redundancy weight depending upon the position of the pixel and the source position. The commonly used FDK-type algorithm with short scan weighting applies weighting before convolution. Each pixel data needs to be convolved and back-projected. It is much more efficient if redundancy weighting is applied after convolution, as data needs to be convolved only once for all image pixels, and redundancy weighting is applied during back-projection step. In R. Grimmer, M. Oelhafen, U. Elstrom, and M. Kachelriess, CT Reconstruction with Extended z-Range, *Conf. Record of IEEE NSS-MIC*, October 2008, this is achieved by rebinning data to parallel geometry. In the present invention, the algorithm proposed in A. A. Zamyatin, K. Taguchi and M. D. Silver, Practical Hybrid Convolution Algorithm for Helical CT Reconstruction, *IEEE Transactions on Nuclear Sciences*, vol. 53, no. 1, pages 167-174, which is herein incorporated by reference, is used, which allows switching the order of weighting and convolution without rebinning to parallel geometry.

Figure 8:
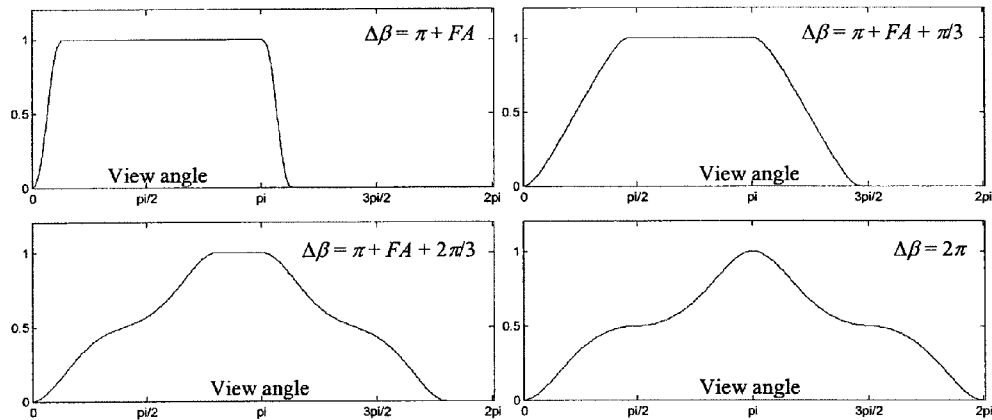
FIGS. 8 and 9 shows central channel profiles of the weight for different view ranges and different values of the smoothing interval, respectively.
Figure 9:
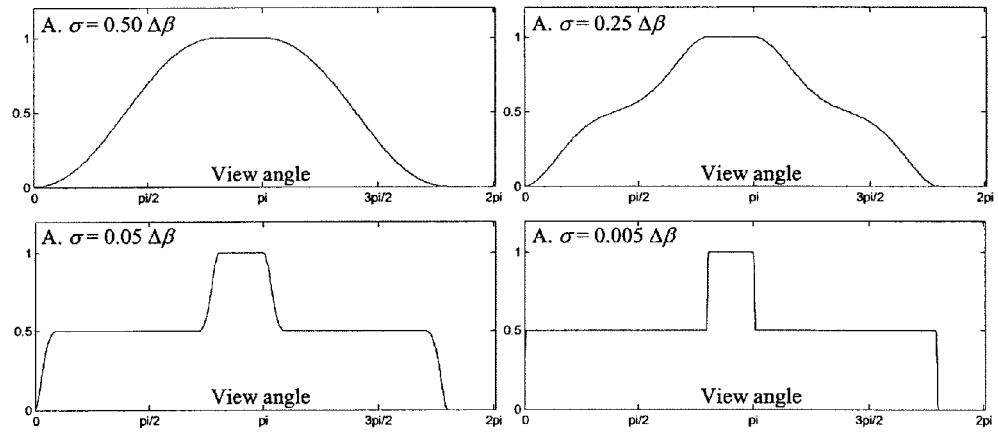

The preferred redundancy weighting function is described in F. Noo, M. Defrise, R. Clackdoyle and H. Kudo, Image reconstruction from fan-beam projections on less than a short scan, *Phys. Med. Biol.*, 47 (2002) 2525-2546, (NDCK weight), given by $$w_N(\beta, \gamma) = \frac{c(\beta)}{\sum_{n=-N}^{N} c(\beta_n, \gamma_n)} \quad (20)$$

$$(\beta_n, \gamma_n) = \begin{cases} (\beta + \pi n, \gamma) & n \text{ is even} \\ (\beta + \pi n + 2\gamma, -\gamma) & n \text{ is odd,} \end{cases} \quad (21)$$

where N=1, 2, . . . is the number of 1π arcs used for image reconstruction, and the function c(β) is given by:

$$c(\beta) = \begin{cases} \cos^2 \frac{\pi(\beta_{start} + \sigma - \beta)}{2\sigma}, & \beta_{start} \leq \beta \leq \beta_{start} + \sigma \\ 1, & \beta_{start} + \sigma \leq \beta \leq \beta_{end} - \sigma \\ \cos^2 \frac{\pi(\beta - \beta_{end} + \sigma)}{2\sigma}, & \beta_{end} - \sigma \leq \beta \leq \beta_{end} \end{cases} \quad (22)$$

where σ is the smoothing interval. FIG. 8 shows central channel profiles of the weight for different view ranges. FIG. 9 shows central channel profiles of the weight for different values of the smoothing interval σ. Note that as σ→0, short scan weight transforms into full scan weight. Therefore, near the edge of the 2π range it is desired to use a small σ. Note also that smaller σ results in better noise performance. However, if σ is too small, weighting becomes non-smooth which may lead to streak artifacts. On the other hand, when extrapolated data is used, it is better to put a small weight on extrapolated data at the ends of the view-range, and therefore it is better to use a larger value of σ.

FIG. 8 shows that the range of the redundancy weighting function [$\beta_{start}$, $\beta_{end}$] smoothly varies from full-scan near the edge of the FS region to 1π half-scan for the pixels near the edge of HS region. FIG. 9 shows that the shape of the redundancy weighting function smoothly varies from full-scan near the edge of the FS region to 1π short-scan for the pixels near the edge of HS region.

Therefore, is it preferable to make σ variable, depending on the view range Δβ(r,z). If Δβ(r,z) is close to 2π, then make σ is made small, for example σ=0.05×Δβ(r,z). If, on the other hand, as $\Delta\beta(r,z)$ approaches $\Delta\beta_\pi(r)$, then, preferably, $\sigma \to 0.5 \times \Delta\beta(r,z)$. In other words, $\sigma$ can be found by:

$$\sigma = k(\Delta\beta(r,z)) \times \Delta\beta(r,z)$$

$$k(\Delta\beta(r,z)) = k_{min} + \frac{\Delta\beta(r,z) - \Delta\beta_\pi(r)}{2\pi - \Delta\beta_\pi(r)} (k_{max} - k_{min}) \quad (22)$$

where $k_{min} = 0.05$ and $k_{max} = 0.5$.

Preferably, a pre-computed weight table is used. Finding the weight value is preferably accomplished by table look-up.

Extrapolated data is obtained outside the FS region, as shown in FIG. 2 above. In some regions the extrapolated FS data overlaps the PBS data. In the overlapping region, the image subvolumes are smoothly feathered to improve image quality by using a weighted sum:

$$\text{Img} = w \times \text{Img}_{ExtFS} + (1-w) \times \text{Img}_{PBS}.$$

At the edge of the extended region with the FS region, w=1, at the edge of the extended region and the PBS region, w=0, and w smoothly varies in between. A linear or smooth non-linear (for example polynomial $3x^2 - 2x^3$, or trigonometric) function may be used. Thus, a smooth, gapless transition is obtained between the FS and PBS regions.

Figure 10:
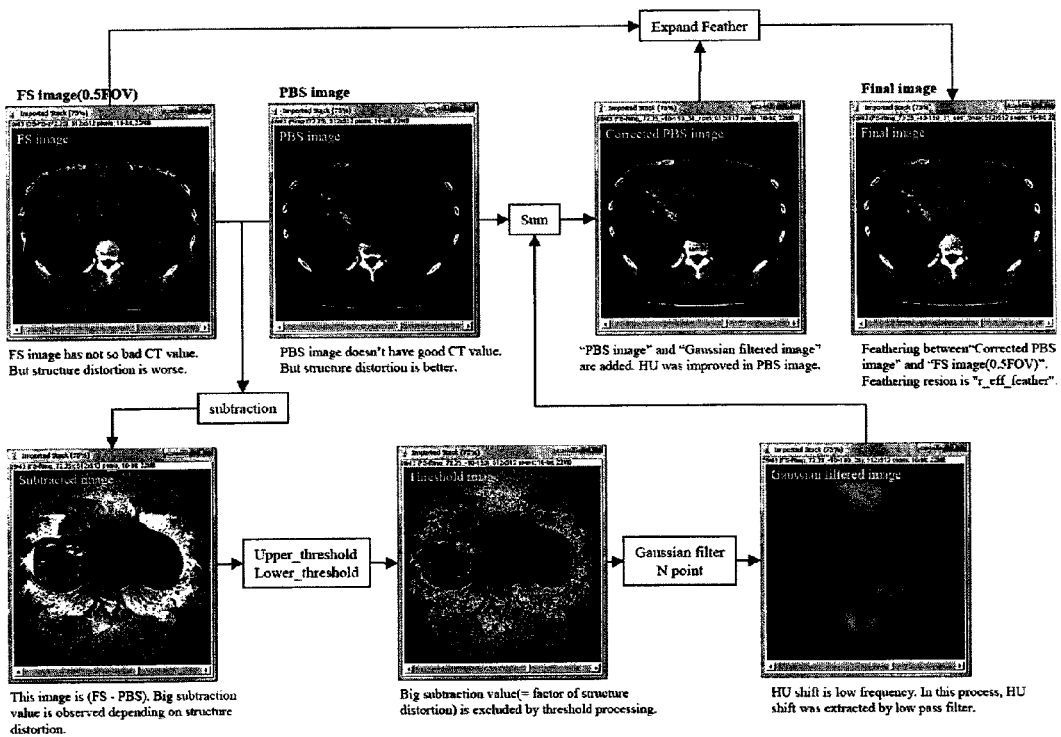
FIG. 10 is a diagram of a second embodiment of the invention.

A second embodiment of the invention is shown in FIG. 10. This embodiment achieves better HU uniformity and improves image quality in the extrapolated region. Additional correction is applied according to the flowchart of FIG. 10. Using the methods described above, an FS image 70 and a PBS image 71 are obtained. The FS image has reasonable quality CT value but has structural distortion. The PBS image has lower quality CT value but less structural distortion. The images are subtracted (FS from PBS) to produce a subtracted image 72. Subtracted image 72 has various subtraction values depending upon the structure distortion. Subtracted image 72 is subjected to thresholding to produce a thresholded image 73. The thresholding operation uses upper and lower thresholds selected to exclude the structure distortion. Thresholded image 73 is then subjected to N point Gaussian filtering to produce a Gaussian filtered image 74. Thresholded image 73 has high and low frequency components. The HU shift is low frequency, so a high frequent component is removed by Gaussian filter (Low pass filter). Image 74 has an HU shift in low frequency. The HU shift is extracted by filtering image 74 is then added to the PBS image 71 to produce a corrected PBS image 75 having improved HU value. The corrected PBS image 75 is then used in the feathering process described above to feather the extended and PBS regions to create the final image 76 having improved image quality.

Figure 11:
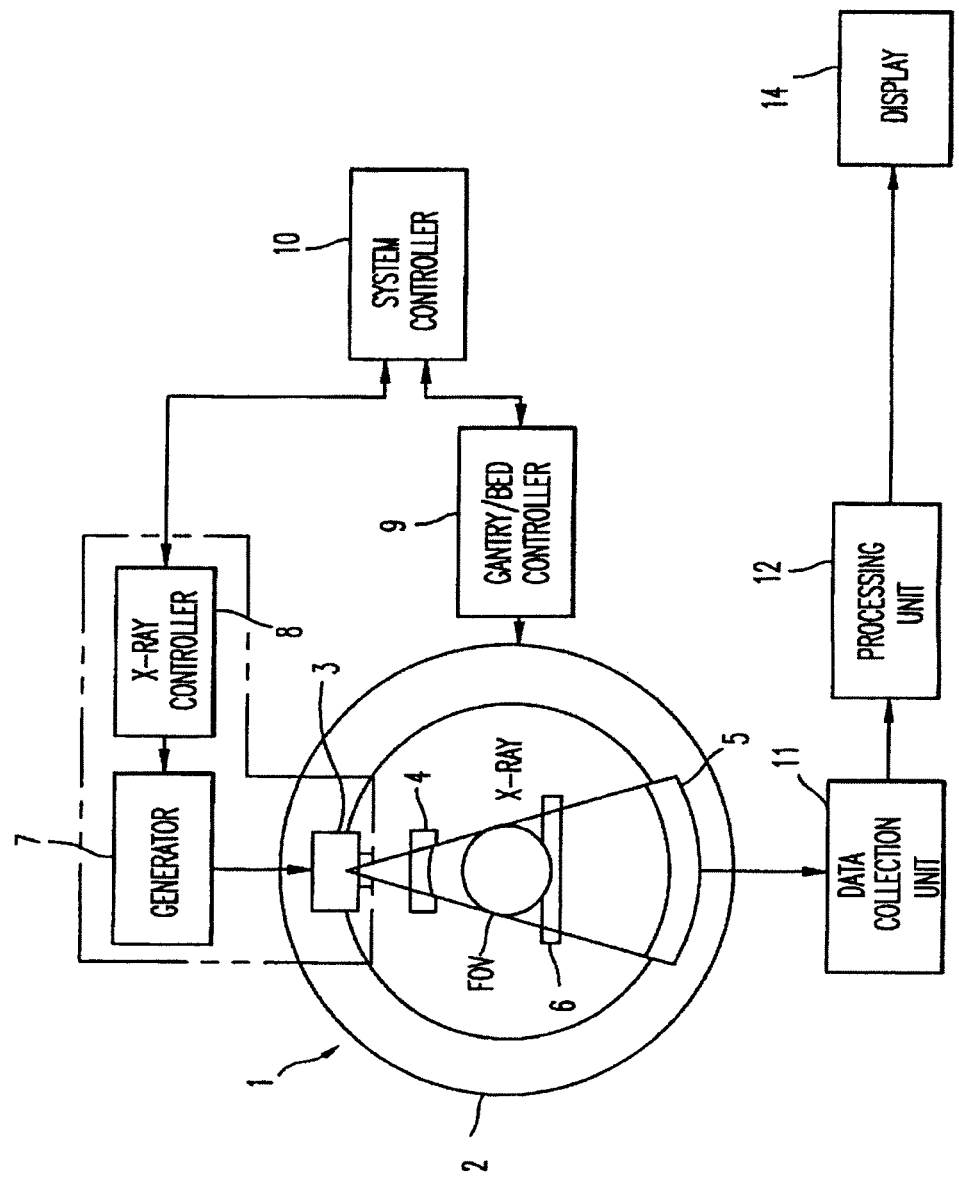
FIG. 11 is a diagram a system according to the invention.

FIG. 11 shows an x-ray computed tomographic imaging device according to the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sidl'es of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3. The source may also be scanned circularly.

The output signal of two-dimensional array type x-ray detector 5 is amplified by a data collection unit 11 for each channel and converted to a digital signal, to produce projection data. The projection data output from data collection unit 11 is fed to processing unit 12. Processing unit 12 performs various processing described above using the projection data. Unit 12 performs interpolation, backprojection and reconstruction, as described above, on the FS, extended and PBS regions to produce the improved image with full rectangular FOV. Unit 12 determines backprojection data reflecting the x-ray absorption in each voxel. In the helical scanning system using a cone-beam of x-rays, the imaging region (effective field of view) is of cylindrical shape of radius o) centered on the axis of revolution. Unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Figure 12:
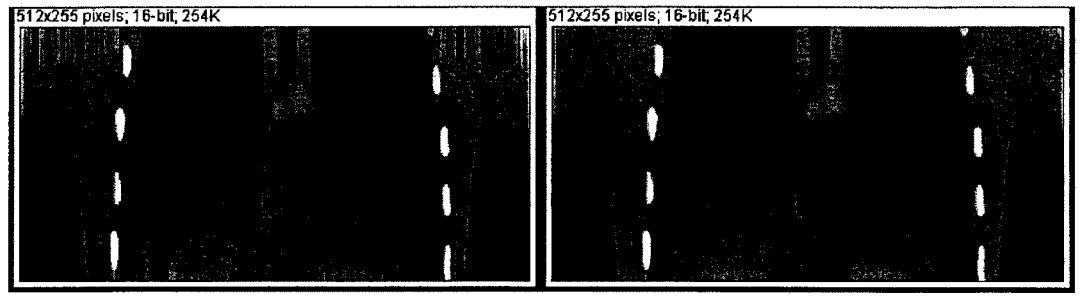

An example of the invention is shown in FIG. 12. Here, a torso phantom was exposed to x-rays using a detector with 256 rows and 0.5 mm detector cell width. The left image is conventional FDK-FS reconstruction and the right image is the method according to the invention. The conventional image has strong artifacts in the corners due to insufficient data.

Figure 13:
Figure 14:
Figure 15:

Another example is shown in FIGS. 13-15. A 320 row detector with 0.5 mm detector width was used. In each figure the left image is the conventional FDK-FS processing and the right image is the processing according to the invention. In FIG. 13 the missing regions are masked in the conventional image and the image processed according to the invention has greater coverage and detail. The images of FIGS. 14 and 15 show the hexagonal FOV of the conventional image and the rectangular FOV of the image processed according to the invention. The images according to the invention exhibit good CT values with no shape distortion in the PBS regions.

The invention may also be embodied in the form a computer-readable medium containing a stored program to cause a computer to carry out the various operations and functions described above.

Numerous other modifications and variations of the present invention are possible in light of the above teachings. This document and equations have been developed for a curved detector array. For example, a flat or other detector array shape can be implemented. Images can be reconstructed either in native cone-beam (CB) or rebinned cone-parallel (CP) geometry. CP geometry offers computational simplicity, but loses spatial resolution due to the additional re-sampling step that uses interpolated data. Using CB geometry better preserves the spatial resolution.

It is therefore to be understood that within the scope of the appended claims, the invention may be practiced otherwise than as specifically described herein.

The invention claimed is:

1. A computed-tomography method, comprising:
   scanning an object with x-rays to obtain projection data;
   reconstructing a first part of an image of the object where full scan data is available;
   reconstructing a second part of the image using half-scanning where full scan data is not available;
   reconstructing a third part of the image using data extrapolated from the full scan data;
   combining weighted sums of overlapping portions of the second and third parts; and
   obtaining the image using the first to third parts and the combined weighted sums.

2. A method as recited in claim 1, wherein an angular range of the half-scanning for a pixel located at (r, φ) is given by:

$$\beta_{start}(r,\phi,z)=\phi+\pi-\Delta\beta(r,z)/2$$

$$\beta_{end}(r,\phi,z)=\phi+\pi+\Delta\beta(r,z)/2=\beta_{start}(r,\phi,z)+\Delta\beta(r,z)$$

where:

$$\Delta\beta(r,z)=\pi+2\theta$$

$$\theta = \frac{\pi}{2} - \phi, \phi = \arcsin\left(\frac{d}{R}\sin\gamma\right)$$

$$\gamma = \arccos\left(\frac{r^2 + d^2 - R^2}{2rd}\right) \text{ and}$$

$$d = R\frac{z}{W},$$

with:
R being a distance from an x-ray source to a center an x-ray detector,
W being a half-width of the detector at the center of the x-ray detector, and
z is an axial direction of the object.

3. A method as recited in claim 1, comprising:
   applying redundancy weighting to each pixel.

4. A method as recited in claim 3, wherein applying redundancy weighting to said pixels comprises using:

$$w_N(\beta, \gamma) = \frac{c(\beta)}{\sum_{n=-N}^{N} c(\beta_n, \gamma_n)}$$

where:

$$(\beta_n, \gamma_n) = \begin{cases} (\beta + \pi n, \gamma) & n \text{ is even} \\ (\beta + \pi n + 2\gamma, -\gamma) & n \text{ is odd,} \end{cases}$$

N=1, 2, . . . and is a number of 1π arcs used for image reconstruction, $$c(\beta) = \begin{cases} \cos^2 \frac{\pi(\beta_{start} + \sigma - \beta)}{2\sigma}, & \beta_{start} \leq \beta \leq \beta_{start} + \sigma \\ 1, & \beta_{start} + \sigma \leq \beta \leq \beta_{end} - \sigma \\ \cos^2 \frac{\pi(\beta - \beta_{end} + \sigma)}{2\sigma}, & \beta_{end} - \sigma \leq \beta \leq \beta_{end}, \end{cases}$$

$\sigma = k(\Delta\beta(r,z)) \times \Delta\beta(r,z)$, and $$k(\Delta\beta(r, z)) = k_{min} + \frac{\Delta\beta(r, z) - \Delta\beta_\pi(r)}{2\pi - \Delta\beta_\pi(r)}(k_{max} - k_{min}),$$

for $k_{min}$=0.05 and $k_{max}$=0.5.

5. A method as recited in claim 3, wherein the redundancy weighting is dependent upon angular positions of reconstruction pixels.

6. A method as recited in claim 3, wherein the redundancy weighting is dependent upon radial positions of reconstruction pixels.

7. A method as recited in claim 3, wherein the redundancy weighting is dependent upon a z-direction position of reconstruction pixels.

8. A method as recited in claim 1, comprising:
   determining a first portion of the second part which overlaps a first portion of the third part;
   combining weighted sums of the first portions to produce a fourth part;
   determining second portions of the second and third parts which do not overlap; and
   obtaining the image using the first part, second portions and the fourth part.

9. A method as recited in claim 1, wherein said combining comprises:
   feathering together said second and third parts.

10. A method as recited in claim 9, comprising:
    assigning a weight w=1 to data located at a first border between said first and second parts;
    assigning a weight w=0 to data located at a second border between said second and third parts;
    smoothly varying said weight w between 0 and 1 across said second part;
    combining said second and third parts using:

Img=w×Img2+(w−1)×Img3, where Img is a combined image, Img2 is image data from said second part and Img3 is image data from said third part at a given pixel.

11. A method as recited in claim 10, comprising combining weighted sums of overlapping portions of the first and second parts.

12. A method as recited in claim 11, wherein data is extrapolated over a region of said image adjacent to where said full scan data is available and which overlaps said half-scan data, said method comprising:
    assigning a weight w=1 to data located at one edge of said region adjacent to said full scan data;
    assigning a weight w=0 to data located at the farthest extent of said region intersecting with said half-scan data;
    smoothly varying said weight w between 1 and 0 across said region;
    combining said second and third parts using:

Img=w×Img2+(w−1)×Img3, where Img is a combined image, Img2 is extrapolated image data and Img3 is half-scan at a given pixel.

13. A computed-tomography apparatus, comprising:
an x-ray source;
an x-ray detector; and
a reconstruction processor for reconstructing an image of an subject from data collected by said x-ray detector, wherein the processor
reconstructs a first part of the image where full scan data is available;
reconstructs a second part of the image using half-scanning data where full scan data is not available;
reconstructs a third part of the image using data extrapolated from the full scan data;
combines weighted sums of overlapping portions of the second and third parts; and
reconstructs the image using the first to third parts and combined weighted sums.

14. An apparatus as recited in claim 13, comprising:
wherein said processor applies redundancy weighting to each pixel.

15. An apparatus as recited in claim 14, wherein said processor applies redundancy weighting to said pixels comprises using:

$$w_N(\beta, \gamma) = \frac{c(\beta)}{\sum_{n=-N}^{N} c(\beta_n, \gamma_n)}$$

where:

$$(\beta_n, \gamma_n) = \begin{cases} (\beta + \pi n, \gamma) & n \text{ is even} \\ (\beta + \pi n + 2\gamma, -\gamma) & n \text{ is odd,} \end{cases}$$

N=1, 2, . . . and is a number of $1\pi$ arcs used for image reconstruction, $$c(\beta) = \begin{cases} \cos^2 \frac{\pi(\beta_{start} + \sigma - \beta)}{2\sigma}, & \beta_{start} \leq \beta \leq \beta_{start} + \sigma \\ 1, & \beta_{start} + \sigma \leq \beta \leq \beta_{end} - \sigma \\ \cos^2 \frac{\pi(\beta - \beta_{end} + \sigma)}{2\sigma}, & \beta_{end} - \sigma \leq \beta \leq \beta_{end}, \end{cases}$$

$\sigma = k(\Delta\beta(r,z)) \times \Delta\beta(r,z)$, and $$k(\Delta\beta(r, z)) = k_{min} + \frac{\Delta\beta(r, z) - \Delta\beta_\pi(r)}{2\pi - \Delta\beta_\pi(r)}(k_{max} - k_{min}),$$

for $k_{min}$=0.05 and $k_{max}$=0.5.

16. An apparatus as recited in claim 15, wherein the redundancy weighting is dependent upon angular positions of reconstruction pixels.

17. An apparatus as recited in claim 15, wherein the processor applies redundancy weighting dependent upon radial positions of reconstruction pixels.

18. An apparatus as recited in claim 15, wherein the processor applies redundancy weighting dependent upon a z-direction position of reconstruction pixels.

19. An apparatus as recited in claim 15, comprising:
determining a first portion of the second part which overlaps a first portion of the third part;
combining weighted sums of the first portions to produce a fourth part;
determining second portions of the second and third parts which do not overlap; and
obtaining the image using the first part, second portions and the fourth part.

20. An apparatus as recited in claim 13, wherein said processor feathers together said second and third parts.

21. An apparatus as recited in claim 13, wherein said processor:
assigns a weight w=1 to data located at a first border between said first and second parts;
assigns a weight w=0 to data located at a second border between said second and third parts;
smoothly varies said weight w between 0 and 1 across said second part; and
combines said second and third parts using:

Img=w×Img2+(w−1)×Img3, where Img is a combined image, Img2 is image data from said second part and Img3 is image data from said third part at a given pixel.

* * * * *